United States Patent
Tepe

(10) Patent No.: US 7,132,468 B2
(45) Date of Patent: Nov. 7, 2006

(54) THICKENER FOR HIGH-SURFACTANT AQUEOUS SYSTEMS

(75) Inventor: Thomas Richard Tepe, King of Prussia, PA (US)

(73) Assignee: Rohm and Haas Company, Philadelphia, PA (US)

(*) Notice: Subject to any disclaimer, the term of this patent is extended or adjusted under 35 U.S.C. 154(b) by 96 days.

(21) Appl. No.: 10/665,329

(22) Filed: Sep. 18, 2003

(65) Prior Publication Data

US 2004/0063855 A1 Apr. 1, 2004

Related U.S. Application Data

(60) Provisional application No. 60/414,587, filed on Sep. 30, 2002.

(51) Int. Cl.
*C08K 3/34* (2006.01)
*C08L 33/06* (2006.01)
*A61K 8/81* (2006.01)

(52) U.S. Cl. ............... 524/446; 524/445; 524/560; 524/561; 526/318.41; 424/70.16

(58) Field of Classification Search ............... 524/445, 524/446, 560, 561; 424/70.16; 526/318.41
See application file for complete search history.

(56) References Cited

U.S. PATENT DOCUMENTS 4,351,754 A 9/1982 Dupre
4,657,943 A 4/1987 Wietsma
5,057,241 A * 10/1991 Merritt et al. ............... 510/428
5,587,154 A * 12/1996 Dowell et al. ........... 424/70.11
5,656,257 A * 8/1997 Fealy et al. ............. 424/70.13
6,559,970 B1 5/2003 Yamamoto et al.
6,695,887 B1 * 2/2004 Cottard et al. ................. 8/405
2002/0035070 A1 * 3/2002 Gardlik et al. ................ 514/23

FOREIGN PATENT DOCUMENTS

WO WO 01 19946 A 3/2001
WO WO 02 65996 A 8/2002

OTHER PUBLICATIONS

Joseph Laryea et al.; Stabilized Shampoo/Surfactant Suspensions; *Kenneth Mason Publications Ltd.*; vol. 434, pp. 1032-1033 (copied onto 4 pages); (Jun. 2000).
M Coccia et al.; "Interactions between hydrophobically modified water dispersible rheology modifiers and surfactants in household detergent applications"; *proceedings 5th World Surfactants Congress, Firenze, Italy*; p. 1271 and pp. 1287-1296, tables 4,5; (2000).

* cited by examiner

*Primary Examiner*—Vasu Jagannathan
*Assistant Examiner*—Vickey Ronesi
(74) *Attorney, Agent, or Firm*—Kenneth Crimaldi

(57) ABSTRACT

An aqueous composition comprising at least 18% surfactant and colloidal inorganic clay. This composition is stable with regard to phase separation at 40° C. for at least three months and exhibits increased low-shear viscosity relative to a composition without clay. The composition comprises at least one lipophilically-modified copolymer containing acrylic acid residues and $C_2$–$C_4$ alkyl (meth)acrylate residues.

7 Claims, No Drawings

THICKENER FOR HIGH-SURFACTANT AQUEOUS SYSTEMS

CROSS REFERENCE TO RELATED PATENT APPLICATIONS

This is a non-provisional application of prior pending U.S. provisional application Ser. No. 60/414,587 filed Sep. 30, 2002.

This invention relates to an aqueous system having a high surfactant level, a clay thickener and a rheology-modifying polymer.

Thickeners are used in aqueous cleaning products, including for example, shampoo, to increase viscosity at low shear rates while maintaining flow properties of the product at higher shear rates, thus allowing blending, packaging and dispensing of the product. A variety of copolymer thickeners made from vinyl monomers have been used for this purpose, as well as inorganic thickeners, including clay. For example, J. Laryea et al., *Research Disclosure,* June 2000, No. 434, pages 1032–1033, disclose an aqueous composition comprising a surfactant mixture appropriate for a shampoo composition, a synthetic hectorite clay and an acrylic emulsion polymer of methacrylic acid, an alkyl acrylate, acrylic acid and behenyloxypoly(ethyleneoxy)$_{25}$ethyl methacrylate. However, the aqueous composition of this reference has a total surfactant level of only 14.6%. There is no suggestion of how to achieve favorable rheological properties at the higher surfactant levels common in many household and industrial cleaners.

The problem addressed by the present invention is the need for a rheology modifier system having good stability and favorable rheological properties at high surfactant levels.

STATEMENT OF INVENTION

The present invention provides an aqueous composition comprising: (a). ) from 18% to 60% of at least one surfactant; (b) from 0.1% to 10% of at least one copolymer comprising from 2.5% to 30% acrylic acid residues, from 10% to 80% $C_2$–$C_4$ alkyl (meth)acrylate residues, and from 2% to 25% lipophilically modified (meth)acrylate residues; and (c) from 0.08% to 0.9% of a clay.

The present invention further provides an aqueous composition comprising at least 18% surfactant and colloidal inorganic clay. This composition is stable with regard to phase separation at 40° C. for at least three months and exhibits increased low-shear viscosity relative to a composition without clay. The composition comprises at least one lipophilically-modified copolymer containing acrylic acid residues and $C_2$–$C_4$ alkyl (meth)acrylate residues.

DETAILED DESCRIPTION

Percentages are weight percentages based on the entire composition, unless specified otherwise. As used herein the term "(meth)aciylic" refers to acrylic or methacrylic, and "(meth)acrylate" refers to acrylate or methacrylate. The term "acrylic polymers" refers to polymers of acrylic monomers, i.e., acrylic acid (AA), methacrylic acid (MAA) and their esters, and copolymers comprising at least 50% of acrylic monomers. Esters of AA and MAA include, but are not limited to, methyl methacrylate (MMA), ethyl methacrylate (EMA), butyl methacrylate (BMA), hydroxyethyl methacrylate (HEMA), methyl acrylate (MA), ethyl acrylate (EA), butyl acrylate (BA), and hydroxyethyl acrylate (HEA), as well as other alkyl esters of AA or MAA, including the lipophilically modified monomers described below. Preferably, acrylic polymers have at least 75% of monomer residues derived from (meth)acrylic acid or (meth)acrylate monomers, more preferably at least 90%, more preferably at least 95%, and most preferably at least 98%. The term "vinyl monomer" refers to a monomer suitable for addition polymerization and containing a single polymerizable carbon-carbon double bond. Monomer residue amounts are expressed as weight percentages.

The lipophilically-modified copolymer used according to the invention contains lipophilically-modified (meth)acrylate residues each of which may contain either one, or a plurality of, lipophilic groups. According to one embodiment, such groups are suitably in the same copolymer component as and attached to hydrophilic chains, such as for example polyoxyethylene chains. According to another embodiment, the copolymer may contain a vinyl group which may be used to copolymerize the polymer to other vinyl-containing entities to alter or improve the properties of the polymer. Alternatively other copolymerization systems may be used. The polymerizable group may be attached to the lipophilic group directly, or indirectly for example via one or more, for example up to 60, preferably up to 40, water-soluble linker groups, for example, —CH[R]CH$_2$O— or —CH[R]CH$_2$NH— groups wherein R is hydrogen or methyl. Alternatively, the polymerizable group may be attached to the lipophilic group by reaction of the hydrophilic, for example polyoxyethylene, component with a urethane compound containing unsaturation. The molecular weight of the lipophilic-modifying group or groups is preferably selected together with the number of such groups to give the required minimum lipophilic content in the copolymer, and preferably, for satisfactory performance in a wide range of systems.

The amount of lipophilically-modified component in the copolymers useful in the present invention preferably is at least 5%, more preferably at least 7.5%, and most preferably at least 10%; and preferably is no more than 25%, more preferably no more than 20%, more preferably no more than 18%, and most preferably no more than 15%.

The lipophilic-modifying groups themselves are preferably straight chain saturated alkyl groups, but may be aralkyl or alkyl carbocyclic groups such as alkylphenyl groups, having at least 6, and up to 30 carbon atoms although branched chain groups may be contemplated. It is understood that the alkyl groups may be either of synthetic or of natural origin and, in the latter case particularly, may contain a range of chain lengths. For example, naturally sourced stearic acid, even of commercially pure quality may contain only about 90% of stearic chains, up to about 7% of palmitic chains and a proportion of other chains and lower quality products may contain substantially less stearic acid. It is intended herein that reference to the chain length of such groups is to the predominant chain length which is present as more than 50%, preferably in more than 75%, of the chains.

It is an important subsidiary feature of the invention that the chain length of the lipophilic-modifying groups be minimized and the alkyl chain length, or predominant chain length, preferably is below 25, more preferably from 8 to 22, and most preferably from 10 to 18 carbon atoms. The hydrophilic component of the lipophilically-modified copolymer may suitably be a polyoxyethylene component preferably comprising at least one chain of at least 2, preferably at least 5, more preferably at least 10, and up to 60, preferably up to 40, more preferably up to 30 ethylene oxide units. Such components are usually produced in a mixture of chain lengths.

Preferably, the $C_2$–$C_4$ alkyl (meth)acrylate residues in the copolymer used in this invention are $C_2$–$C_3$ alkyl (meth) acrylate residues, and most preferably EA. Preferably, the amount of $C_2$–$C_4$ alkyl (meth)acrylate residues is at least 20%, more preferably at least 30%, more preferably at least 40% and most preferably at least 50%. Preferably, the amount of $C_2$–$C_4$ alkyl (meth)acrylate residues is no more than 75%, more preferably no more than 70%, and most preferably no more than 65%. Preferably, the amount of acrylic acid residues in the copolymer used in the present invention is at least 5%, more preferably at least 7.5%, more preferably at least 10%, and most preferably at least 15%. Preferably, the amount of acrylic acid residues is no more than 27.5%, more preferably no more than 25%, and most preferably no more than 22%. Acrylic acid residues are introduced into the copolymer by inclusion of either acrylic acid, or an acrylic acid oligomer having a polymerizable vinyl group, in the monomer mixture used to produce the copolymer. Preferably, the copolymer contains residues derived from methacrylic acid in an amount that provides a total acrylic acid plus methacrylic acid content of at least 15%, more preferably at least 17.5%, and most preferably at least 20%. Preferably, the total acrylic acid plus methacrylic acid content of the copolymer is no more than 65%, more preferably no more than 50%, and most preferably no more than 40%.

Optionally, the copolymer also contains from 2% to 25%, preferably from 5% to 20%, of a hydrophilic comonomer, preferably one having hydroxyl, carboxylic acid or sulfonic acid functionality. Examples of hydrophilic comonomers include 2-hydroxyethyl (meth)acrylate (HEMA or HEA), itaconic acid and acrylamido-2-methylpropanesulfonic acid.

The aqueous compositions of the present invention contain from 0.1% to 10% of at least one copolymer; i.e., the total amount of copolymer(s) is in this range. Preferably, the amount of copolymer in the aqueous composition is at least 0.3%, more preferably at least 0.5%, more preferably at least 0.7%, and most preferably at least 1%. Preferably, the amount of copolymer in the aqueous composition is no more than 7%, more preferably no more than 5%, and most preferably no more than 3%. Preferably, the copolymer is an acrylic polymer. The copolymer, in aqueous dispersion or in the dry form, may be blended into an aqueous system to be thickened followed, in the case of a pH-responsive thickener, by a suitable addition of acidic or basic material if required. In the case of the copolymeric pH-responsive thickeners described above, the pH of the system to be thickened is at, or is adjusted to, at least 5, preferably at least 6, more preferably at least 7; preferably the pH is adjusted to no more than 13. The neutralizing agent is preferably a base such as an amine base or an alkali metal or ammonium hydroxide, most preferably sodium hydroxide, ammonium hydroxide or triethanolamine (TEA). Alternatively, the copolymer may first be neutralized in aqueous dispersion and then blended. The surfactant preferably is blended into the aqueous composition separately from the copolymer prior to neutralization.

Preferably, the clay used in the present invention is a clay having a particle size range in the colloidal range. Typically, such clays provide a clear solution when they are hydrated, possibly because the clay particles do not scatter light when the clay is hydrated and exfoliates. Suitable clays include, for example, synthetic hectorite clays and natural hectorites or bentonites processed to provide complete exfoliation of the platelettes to a colloidal size range. Other larger or less exfoliated clays are expected to also provide low shear viscosity build described herein, but the aqueous compositions will lack clarity. Preferably, the clay is present in the aqueous composition in an amount of at least 0.2%, more preferably at least 0.3%. Preferably, the clay is present in the aqueous composition in an amount of no more than 0.7%, more preferably no more than 0.6%, and most preferably no more than 0.5%.

The aqueous compositions of the present invention contain from 15% to 60% of at least one surfactant; i.e., the total amount of surfactant(s) is in this range. Preferably, the aqueous compositions of the present invention contain at least 20%, more preferably at least 21%, and most preferably at least 22%, of at least one surfactant. Preferably, the aqueous composition contains no more than 50%, more preferably no more than 45%, more preferably no more than 35%, more preferably no more than 30%, and most preferably no more than 25%, of at least one surfactant. The surfactant(s) preferably is selected from the groups of anionic surfactants characterized by carboxylate, sulfonate, sulfate or phosphate solubilizing groups, and nonionic surfactants characterized by amide or hydroxyl groups or ethylene oxide chains. Cationic, amphoteric or zwitterionic surfactants may also or alternatively be used provided that they are compatible with the thickening copolymer and other ingredients of the aqueous system in the quantity required by the invention. Cationic surfactants characterized by amine or ammonium solubilizing groups, and/or amphoteric surfactants characterized by combinations of the anionic and cationic solubilizing groups may be selected. A particularly preferred composition contains an anionic surfactant and a nonionic surfactant, preferably at a ratio from 2.5:1 to 1.5:1, respectively.

Preferred surfactants for use in the practice of the invention may be selected from the $C_8$ to $C_{18}$ fatty acids or their water soluble salts, water soluble sulfates of $C_8$ to $C_{18}$ alcohols, sulfonated alkylaryl compounds such as, for example, dodecylbenzene sulfonate, alkylphenoxy polyethoxy ethanols, for example with $C_7$ to $C_{18}$ alkyl groups and 9 to 40 or more oxyethylene units, ethylene oxide derivatives of long chain carboxylic acids, for example of lauric, myristic, palmitic or oleic acids, ethylene oxide derivatives of long chain alcohols, for example of lauryl or cetyl alcohols, alkanolamides and polyglucosides, for example the alkyl polyglucosides. Suitable cationic surfactants may be, for example, lauryl pyridinium chloride, octylbenzyltrimethyl-ammonium chloride, dodecyl trimethylammonium chloride and ethylene oxide condensates of primary fatty acid amines.

The composition of the present invention optionally may include other ingredients, e.g., dispersants, biocides, dyes, etc. Dispersants may be added to further stabilize the clay against known flocculation behavior, which would undesirably increase viscosity at moderate shear rates. Such dispersants would have surface activity suitable for stabilizing clay particles, including, but not limited to, low-molecular-weight polyacrylic acids and polymaleic acids.

The copolymer may be a pH-responsive thickener. The pH-responsive copolymer thickener systems may be prepared by copolymerizing the monomers using known aqueous or inverse emulsification procedures at an acidic pH, or precipitation or solution polymerization processes, and any other suitable additives known in the art, for example, a free-radical initiator such as a peroxygen compound and, optionally, chain transfer agents. Suitable peroxygen compounds may be peroxides, hydroperoxides, persulfates or organic peroxides and a suitable quantity of initiator may be 0.01% to 3% by weight of the components of the copolymer. The copolymerization temperature may suitable be about 60° C. to 90° C. The copolymer emulsion may be recovered by filtration and the copolymer may, if desired, be provided in dry form by spray, drum or other drying. U.S. Pat. Nos. 4,384,096, 4,663,385, 4,429,097 and 4,514,552 may be consulted for further general and specific details of suitable copolymerization and recovery techniques, and of suitable monomers and additives. The molecular weight of uncrosslinked lipophilically-modified copolymer is typically in the range of about 100,000 to 1 million.

In one embodiment of the invention, the copolymer is crosslinked, that is, a crosslinking agent, such as a monomer having two or more ethylenic unsaturated groups, is included with the copolymer components during polymerization. Examples of such monomers include diallyl phthalate, divinylbenzene, allyl methacrylate, diacrylobutylene or ethylene glycol dimethacrylate. When used, the amount of crosslinking agent is typically from 0.01% to 2%, preferably from 0.1 to 1% and more preferably from 0.2 to 0.8%, based on weight of the copolymer components.

In one embodiment of the invention that the copolymer is prepared in the presence of a chain transfer agent when a crosslinking agent is used. Examples of suitable chain transfer agents are carbon tetrachloride, bromoform, bromotrichloromethane, and compounds having a mercapto group, e.g., long chain alkyl mercaptans and thioesters such as dodecyl-, octyl-, tetradecyl- or hexadecyl-mercaptans or butyl-, isooctyl- or dodecyl-thioglycolates. When used, the amount of chain transfer agent is typically from 0.01% to 5%, preferably from 0.1% to 1%, based on weight of the copolymer components. If the crosslinking agent is used in conjunction with a chain transfer agent, which are conflicting operations for polymerization purposes, not only is exceptional efficiency observed but also very high compatibility with hydrophilic surfactants, as manifested by increased product clarity.

EXAMPLE

Preparation of Test Samples: Several different surfactants and surfactant mixtures were used as a base for the test samples, preferably a mixed 2:1, anionic:nonionic surfactant mixture having a total surfactant concentration of 22.3% solids. The typical order of addition for sample preparation was: addition of pre-diluted polymer latex into a concentrated surfactant base, followed by addition of the clay component, followed by the addition of a neutralizing base to neutralize the polymer in an amount dependent on polymer amount added. Control samples were prepared as described above, but without polymer or clay components (surfactant only), as well as without clay (polymer plus surfactant only). Clay-only controls (clay and surfactant) were also prepared but were not stable (to phase separation) without addition of polymer. Test samples were allowed to stand at ambient temperature for at least 24 hours prior to testing.

Step 1. 90.91 g Stepan Polystep™ A-16-22 (sodium dodecylbenzenesulfonate) and 10 g Shell Neodol™ 25-9 (alcohol ethoxylate) were blended to create a stock solution of 29.7% total surfactant solids at a 2:1 anionic:nonionic ratio. Blending can be done with overhead mixing or on a mechanical roller.

Step 2. With overhead mixing, 3 g of Laponite™ RD powder (synthetic layered silicate hectorite clay, 100% active solids) was added to 97 g deionized (DI) water and stirred until homogeneously dispersed.

Step 3. 75 g of the stock surfactant solution from Step 1 were measured into a 4 oz jar.

Step 4. 5 g of the copolymer latex (at 30% active solids) were measured into a 30 mL vial and diluted with 9.47 g DI water.

Step 5. With overhead mixing, the diluted polymer latex from Step 4 was added slowly to the surfactant solution of Step 3 until homogeneously distributed.

Step 6. With continued mixing, 10 g of the Laponite™ RD solution of Step 2 were added to the surfactant+polymer solution of Step 5. Mixing was continued until homogeneous.

Step 7. With continued mixing, 0.53 g triethanolamine was added to the solution of Step 6, and mixing was continued until homogeneous (ca. 5 minutes). The resulting samples contain 22.3% surfactant, 1.5% copolymer, 0.3% clay, and 0.5% triethanolamine, with the remainder being water.

The following test procedures were used to evaluate the samples:

Controlled shear stress rheological testing (at 25° C.) was performed in order to generate a viscosity versus shear stress flow curve. This measurement allowed analysis of the viscosity over a wide range of shear rates. It is well understood that solution properties such as suspendability are dictated by the viscosity in the low shear stress/rate region. However, pourability is correlated to the viscosity at more moderate stresses/rates.

Suspendability: Through Stokes law, one can use the low shear viscosity to calculate what particle density/radius combination can be suspended. As a practical test, however, and to allow us to test the systems under increased temperature, a small amount of Amberlite™ XAD1180 ion exchange resin beads was incorporated into the surfactant solutions, dispersed, and then placed in a 40° C. oven in 1 ounce (30 mL) vials. These beads have a density of 1.03-1.08 and a diameter of ~0.5 mm, with significant variation. Samples were occasionally checked to determine whether the beads remained suspended, with suspension failure defined as gross settling of the beads, typically within a relatively short time frame (hours in some cases). Successful systems kept the beads suspended for at least 3 months with no sign of settling.

Solution clarity: A sample was taken and the turbidity of the solution was measured in Nephelometric Turbidity Units (NTUs). A qualitative measure also was made based on whether the ion exchange resin beads were observable through the vial containing the sample.

Overall results: Initial studies used 1.5% solids of the chosen copolymer, with either 0.04% or 0.08% Laponite™ RD clay. Subsequently a subset of the best performing polymers was formulated using a wider range of clay concentrations (0.005-0.5%). This subset of leads was run in parallel with other polymers that showed some percent increase in low-shear viscosity with addition of clay. The rheology performance combined with the heat-aged suspending results suggested a second criterion that can be used to describe this synergistic effect, i.e., the slope of the curve at the lowest stresses measured. This slope can be considered an indication of the possibility of extrapolating to low stresses beyond the machine limits. Products that may have shown some synergy based on the % change in low shear viscosity but failed under the bead suspension test were noted to show a near zero slope in the low shear regime (i.e., Newtonian behavior). Successful samples showed the synergy in the % change in low shear viscosity, and further showed a significant negative slope in the low shear region. Results are shown in Tables 1 and 2. The copolymer compositions are in weight percent of each monomer, with DAP and nDDM amounts calculated as percentages of the total of the other monomers. Viscosities are given in poise. Shear stresses are in dyne/cm$^2$ ("d/cm$^2$"). All polymers described herein produced stable compositions that showed no visible phase separation on standing at room temperature and at 40° C. for at least three months. Prepared samples that did show phase separation were observed to have a white/opaque gelled phase at the bottom of the sample. No testing was performed on these unstable systems.

Typically, the composition of this invention synergistically increases the low shear (e.g., suspending or stabilizing) viscosity significantly while having little effect on the mid-shear (pouring) viscosity. The effect at low shear can be partially described by calculating the percent change in the viscosity measured at the lowest applied shear stress (machine limit of 0.6 dyne/cm$^2$) for the sample with added clay (polymer+clay) versus the clay-free analog (just polymer).

Table 1 includes data comparing the effect on viscosity of adding 0.08% Laponite™ clay to the composition. The percent change in viscosity is shown in column 4 at a shear stress of 0.6 dyne/cm$^2$, and in column 7 for a shear stress of ca. 1000 dyne/cm$^2$. The latter shear stress corresponds to pouring of a liquid. Column 8 contains measurements of turbidity in NTU. It is readily apparent that copolymers having acrylic acid in combination with a substantial amount of methyl acrylate (last three rows) display both an unfa-

TABLE 1

| copolymer composition | viscosity@ 0.6 d/cm$^2$ (no clay) | viscosity@ 0.6 d/cm$^2$ (0.08% clay) | viscosity change, % | viscosity@ ca. 1000 d/cm$^2$ (no clay) | viscosity@ ca. 1000 d/cm$^2$ (0.08% clay) | viscosity change, % | NTU with clay |
|---|---|---|---|---|---|---|---|
| 70EA/20AA/10Lipo1[a] | 78.1 | 173.1 | 121.6 | 25.8 | 34.0 | 31.8 | 37.3 |
| 60EA/25MAA/5AA/10 Lipo1[a]//0.2DAP[c]//0.1nDDM[d] | 62.6 | 125.8 | 101.0 | 20.6 | 26.4 | 28.2 | 53.1 |
| 60EA/10MAA/20AA/10 Lipo1[a]//0.2DAP[c]//0.1nDDM[d] | 119.0 | 206.5 | 73.6 | 23.3 | 26.9 | 15.5 | 95.3 |
| 47EA/35MAA/18Lipo2[b]//0.5DAP[c]//0.2nDDM[d] | 74.0 | 120.9 | 63.5 | 28.9 | 33.3 | 15.2 | 29.2 |
| 60EA/10MAA/20AA/10Lipo1[a]//0.1DAP[c] | 91.2 | 135.9 | 49.0 | 22.6 | 24.1 | 6.6 | 77.2 |
| 42EA/40MAA/18Lipo1[a]//0.2DAP[c] | 125.3 | 148.7 | 18.6 | 24.8 | 29.4 | 18.5 | 84.5 |
| 50EA/40MAA/10Lipo1[a] | 116.0 | 129.4 | 11.6 | 29.7 | 31.0 | 4.4 | 42.0 |
| 60MA/10MAA/20AA/10Lipo1[a] | 73.6 | 75.9 | 3.2 | 22.1 | 21.9 | −0.9 | 242.0 |
| 60MA/10MAA/20AA/10Lipo2[b] | 152.6 | 141.2 | −7.4 | 28.4 | 28.0 | −1.4 | 173.0 |
| 60MA/10MAA/20AA/10Lipo3[e] | 91.3 | 73.0 | −20.1 | 19.7 | 18.8 | −4.6 | 332.0 |

[a] Lipo1 is a lipophilically modified monomer having a linear saturated $C_{18}$ alkyl group connected through 20 oxyethylene residues to a methacryloyl group.
[b] Lipo2 is a lipophilically modified monomer having a linear saturated $C_{12}$ alkyl group connected through 23 oxyethylene residues to a methacryloyl group.
[c] DAP is diallyl phthalate.
[d] nDDM is n-dodecyl mercaptan.
[e] Lipo3 is a lipophilically modified monomer having a linear saturated $C_{22}$ alkyl group connected through 25 oxyethylene residues to a methacryloyl group.

TABLE 2

| copolymer composition | viscosity@ 0.6 d/cm$^2$ | viscosity@ 2.2 d/cm$^2$ | slope at low shear | resin beads suspended? |
|---|---|---|---|---|
| 50EA/40MAA/10Lipo1[a] | 118.3 | 116.6 | −1.06 | N |
| 47EA/35MAA/18Lipo2[b]//0.5DAP[c]//0.2nDDM[d] | 146.5 | 144 | −1.56 | N |
| 32EA/40MAA/10HEMA/18LiPo2[b]//0.2DAP[c] | 283.9 | 271.8 | −7.56 | N |
| 42EA/40MAA/18Lipo1[a]//0.2DAP[c] | 254 | 236.6 | −10.88 | N |
| 42EA/40MAA/18Lipo1[a]//0.5PEM[e]//0.2DAP[c] | 553.7 | 492.2 | −38.44 | N |
| 60EA/10MAA/20AA/10Lipo1[a]//0.1DAP[c] | 807.4 | 470.5 | −210.56 | Y |
| 60EA/10MAA/20AA/10Lipo1[a] //0.2DAP[c]/0.1nDDM[d] | 958.5 | 536.2 | −263.94 | Y |

[a] Lipo1 is a lipophilically modified monomer having a linear saturated $C_{18}$ alkyl group connected through 20 oxyethylene residues to a methacryloyl group.
[b] Lipo2 is a lipophilically modified monomer having a linear saturated $C_{12}$ alkyl group connected through 23 oxyethylene residues to a methacryloyl group.
[c] DAP is diallyl phthalate.
[d] nDDM is n-dodecyl mercaptan.
[e] PEM is phosphoethyl methacrylate.

vorable viscosity change on addition of clay, and a high turbidity. The first three rows display much better results for copolymers having acrylic acid in combination with ethyl acrylate. Even at a level of 5% acrylic acid (second row), acrylic acid containing copolymers impart favorable viscosity changes with added clay.

Table 2 demonstrates the effect on viscosity of adding 0.5% Laponite™ clay to the composition. The last two entries in Table 2 demonstrate the criticality of acrylic acid residues in the copolymer. At the high surfactant levels described here, many commercially-available rheology modifiers, especially synthetic associative thickeners, lose their capability of building low-shear viscosity without also building viscosity at higher shear rates. In contrast, in the last two samples in Table 2, the viscosity as a function of shear has a much larger negative slope in the low shear range, thus demonstrating continued pseudoplastic behavior to stresses below the resolution limit of the viscometer. These samples have sufficiently high viscosity at low-shear to suspend beads, but still maintain relatively low viscosity at high-shear, allowing mixing and pouring of the composition.

The invention claimed is:

1. An aqueous composition comprising:
   (a) from 18% to 60% by weight of at least one surfactant;
   (b) from 0.1% to 10% by weight of at least one copolymer comprising from 5% to 25% by weight acrylic acid residues, from 40% to 75% by weight ethyl acrylate residues, and from 2% to 25% by weight lipophilically modified (meth)acrylate residues; and further comprising methacrylic acid residues, wherein the acrylic acid plus the methacrylic acid residues total from 20% to 40% by weight of the copolymer; and
   (c) from 0.08% to 0.9% by weight of a clay.

2. The composition of claim 1 having from 20% to 45% by weight of said at least one surfactant.

3. The composition of claim 2 having from 0.3% to 5% by weight of said at least one copolymer and from 0.2% to 0.7% by weight of the clay.

4. The composition of claim 3 in which said at least one copolymer has from 5% to 15% by weight lipophilically modified (meth)acrylate residues.

5. The composition of claim 1 in which the clay has a particle size range in a colloidal range.

6. The composition of claim 5 in which the clay is a synthetic hectorite clay material.

7. An aqueous composition comprising:
   (a) from 20% to 25% by weight of at least one surfactant;
   (b) from 0.5% to 3% by weight of at least one copolymer comprising from 5% to 25% by weight acrylic acid residues, from 40% to 75% by weight ethyl acrylate residues residues, and from 5% to 15% by weight lipophilically modified (meth)acrylate residues; wherein said at least one copolymer further comprises methacrylic acid residues, and the acrylic acid plus the methacrylic acid residues total from 20% to 40% by weight of the copolymer; and
   (c) from 0.08% to 0.5% by weight of a clay.

* * * * *